United States Patent [19]

Gilman

[11] Patent Number: 5,056,510

[45] Date of Patent: Oct. 15, 1991

[54] VENTED WOUND DRESSING

[75] Inventor: Thomas H. Gilman, Mansfield, Mass.

[73] Assignee: The Kendall Company, Mansfield, Mass.

[21] Appl. No.: 461,588

[22] Filed: Jan. 5, 1990

Related U.S. Application Data

[63] Continuation-in-part of Ser. No. 337,591, Apr. 13, 1989.

[51] Int. Cl.$^5$ ............... A61F 13/00; A61F 15/00; A61L 13/00
[52] U.S. Cl. ........................... 128/155; 128/888; 604/307
[58] Field of Search ............ 128/155, 156, 888; 604/304, 307

[56] References Cited

U.S. PATENT DOCUMENTS

| | | | |
|---|---|---|---|
| 1,920,808 | 8/1933 | Sander | 128/156 |
| 2,443,140 | 6/1948 | Larsen | 128/888 |
| 4,399,816 | 8/1983 | Spangler | 128/888 |

Primary Examiner—David J. Isabella
Assistant Examiner—Paul Prebilic
Attorney, Agent, or Firm—Alvin Isaacs

[57] ABSTRACT

A wound dressing comprising a base sheet having an opening for placement over the wound; a vent sheet providing controlled leakage of fluid along a path from the wound through the opening of the base sheet; and a chamber containing a fabric reservoir for receiving and retaining the wound fluid, the walls defining the chamber being constructed so as to provide a complete barrier to bacteria and other external contaminants while at the same time permitting egress of air from the voids or interstices of the fabric reservoir, so as to optimize the wicking and amount of wound fluid which can be retained in the volume provided by the fabric reservoir.

30 Claims, 3 Drawing Sheets

VENTED WOUND DRESSING

REFERENCE TO RELATED APPLICATIONS

This application is a continuation-in-part of my copending application, Ser. No. 337,591 filed Apr. 13, 1989; and is related to my concurrently filed application, Ser. No. 461,598.

BACKGROUND OF THE INVENTION

The parent application, the aforementioned Ser. No. 337,591 is directed to the task of providing an improved wound dressing of simplified construction which maintains a moist environment and prevents scab formation while at the same time obviating the problems which can occur when the wound exudate builds up a pressure bubble beneath the dressing. Such problems include the tendency of the pressure bubble of wound exudate to undermine the adhesive seal to the skin, the resulting increased possibility of contamination of the wound, and the messiness inherent in the escape of wound exudate from the dressing.

In accordance with the invention described and claimed therein, the task is solved in an elegant manner by providing a dressing comprising a base sheet having an opening for placement over the wound; means for securing the base sheet to the skin; and vent means for providing controlled leakage of wound fluid along a path from the wound through the opening of the base sheet, the vent means permitting passage of wound fluid therethrough while reducing evaporation through the opening and thereby helping to insure a moist environment when excess wound fluid is removed from the wound. In a preferred embodiment, the vent means comprises a vent sheet secured to the base sheet over the opening and having a raised portion defining at least one channel extending from the opening to an edge of the vent sheet, the channel communicating with at least one opening permitting the fluid to be vented to the outer surface of the dressing. The opening(s) for venting the fluid may be provided by permitting at least one and preferably two opposed edges of the vent sheet to be free of attachment to the base sheet.

Various embodiments of the vented sheet dressings are described and illustrated in the accompanying drawings.

In the embodiments such as are illustrated in FIGS. 16 and 17 of copending application Ser. No. 337,591 filed Apr. 13, 1989; the wound fluid leaks from the channel through the unsealed edges to the outside of the dressing where it comes in contact with the outside air as well as bacteria or other external contaminants which may be present.

In other embodiments such as are illustrated in FIGS. 1-3, an absorbent layer such as a gauze sponge for receiving and retaining the wound fluid may be located over the back surface of the base sheet and over the vent sheet. As disclosed, a back film of a bacteria impervious material may be secured to the back surface of the absorbent layer.

In still another embodiment, as shown in FIGS. 6 and 7 of copending application Ser. No. 337,591 filed Apr. 13, 1989; a fabric layer impregnated with an antimicrobial agent is secured around its periphery to the back surface of the base sheet. A fluid-impervious cover sheet is secured to the front surface of the fabric layer, i.e. between the fabric layer and the base sheet. The cover sheet is free of attachment to the base sheet and serves as a vent through which fluid can leak and be wicked to the fabric layer.

In summary, the parent case discloses embodiments wherein the wound fluid is present on the outer surface of the dressing. While fully satisfying the objectives of the application in obviating the problems which can occur when wound fluid builds up in and on the wound, it nevertheless is not fully satisfactory in all aspects desired for a wound dressing. Specifically, wound exudate is exposed to the environment as well as to contact with any objects which may be present. Moreover, the outer surface is exposed to bacteria as well as other external contaminants including food or liquid which may be spilled by the patent on the wound, which contaminants can adversely affect the healing process.

In other embodiments, e.g. that shown in FIGS. 1-3, a bacteria-impervious material is disposed over the reservoir for retaining the wound fluid.

While such embodiments will serve to prevent ingress into the dressing of external contaminants, they do present one significant problem, namely the ability for the fabric reservoir to reach its optimum potential for receiving wound fluids.

In order to approximate optimum efficiency of receiving and retaining wound fluids, it is necessary to provide means for removal or displacement of air entrained in the interstices or voids of the fabric reservoir. In other words, it is axiomatic that for one fluid (e.g. wound exudate) to be able to diffuse or wick to a given volume of space, any fluid (e.g. air) initially present in this volume of space must first be permitted to be displaced.

The primary task of this invention is to provide an improved vented dressing of the type described in the parent application, Ser. No. 337,591 having a fabric reservoir for wound fluid disposed over the vent sheet, the fabric reservoir having means protecting it from external contaminants, including bacteria, while at the same time permitting entrained air to be removed so as to optimize the efficiency of the reservoir and, in turn, to minimize the number of dressing changes which may be required.

BRIEF DESCRIPTION OF THE INVENTION

In accordance with this invention the task is solved by employing the teachings of my aforementioned copending application Ser. No. 461,598 to provide a vented dressing wherein the fabric reservoir for wound exudate is contained within a chamber, the walls of which provide an effective barrier to bacteria and other external contaminants, at least a portion of a wall of the chamber being air permeable so as to permit egress of air from within the voids in the fabric reservoir.

DETAILED DESCRIPTION OF THE INVENTION

As heretofore mentioned, the present invention is directed to certain improvements over the vented dressings described and claimed in my copending application Ser. No. 337,591 filed Apr. 13, 1989 of which the instant application is a continuation-in-part, the essence of the invention being providing a fabric reservoir for receiving and retaining wound fluids vented through the dressing, the fabric reservoir being contained within a chamber which is free from external contaminants while, at the same time, permitting displacement of air entrained within the reservoir so as to optimize the ability of the reservoir to receive the wound fluids diffusing thereto.

The novel chamber containing the fabric reservoir is an adaptation of and borrows from the invention described and claimed in my concurrently filed application, Ser. No. 461,598.

The nature and objects of the invention may best be understood from the following detailed description taken in conjunction with the accompanying drawings.

Figure 1:
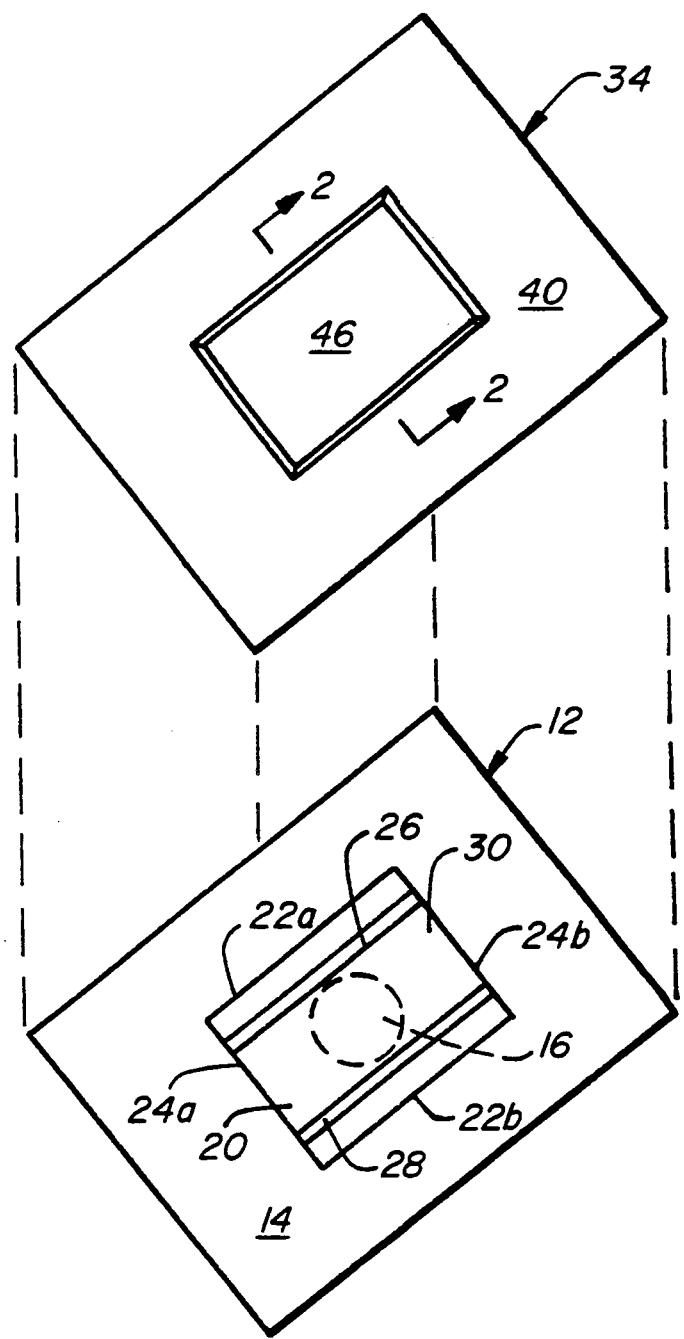
FIG. 1 is an exploded top plan view of the novel wound dressing of this invention.
Figure 2:
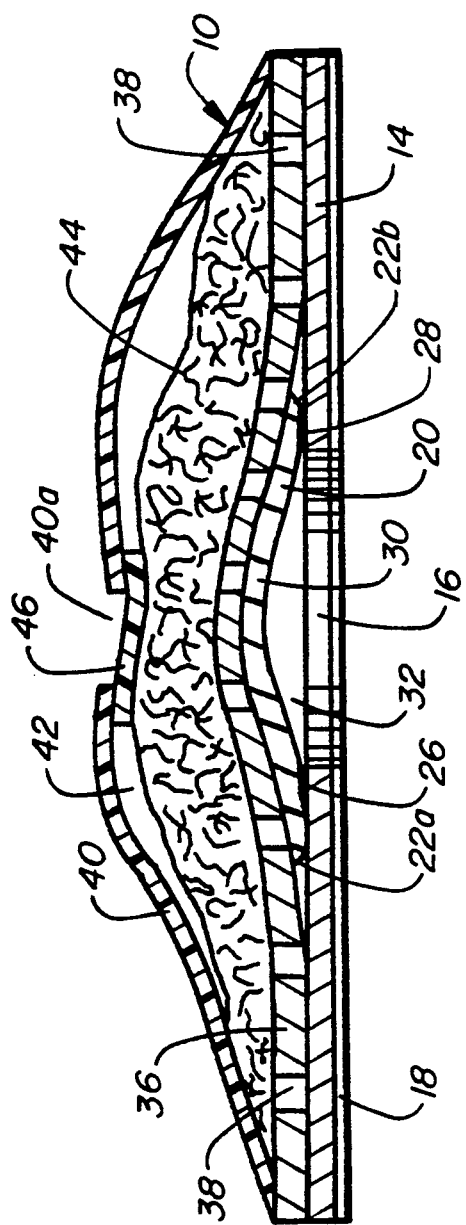
FIG. 2 is a sectional view taken substantially as indicated along the line 2—2 of FIG. 1 with the thicknesses exaggerated for purposes of illustration.

As shown in the FIGS. 1 and 2, the novel wound dressing 10 of this invention consists essentially of a vented dressing component 12 adapted for placement on the wound; and a cover component 34 adapted to receive and to retain wound exudate diffusing from dressing component 12.

Component 12 corresponds essentially to the illustrative embodiment shown in FIGS. 16 and 17 of the aforementioned copending application, Ser. No. 337,591.

Component 12 is illustrated to have a base sheet 14 having an opening 16 extending therethrough. The base sheet has a layer of adhesive 18 on the front surface thereof for securing the dressing 10 to the skin of the patient with the opening 16 over the wound (not shown). The dressing component 12 also has a vent or cover sheet 20 covering the opening 16. The vent sheet 20 has a pair of side edges 22a and 22b and a pair of end edges 24a and 24b connecting the side edges 22a and 22b. While the shape of the vent sheet is not critical and may vary, it preferably is of a generally rectangular configuration. The dressing component 12 has a pair of sealing lines 26 and 28 on either side of opening 16 and extending between the end edges 24a and 24b sealing the cover sheet 20 to the base sheet 14. Sealing lines 26 and 28 may be provided by heat sealing or by means of a suitable adhesive, e.g. a per se known heat or pressure-sensitive adhesive. The vent sheet 20 has an upraised portion or fold 30 located between the sealing lines 26 and 28 defining a channel 32 extending between opening 16 and the end edges 24a and 24b.

In use, when excess pressure builds up due to the presence of wound fluids in the wound, the wound fluid will leak from channel 32 through the unsealed end edges 24a and 24b to the outside or back of base sheet 16, rather than undermining the adhesive layer 18 of the base sheet securing the dressing on the wound.

In accordance with the present invention, the dressing component 12 is provided with a cover component 34 including a fabric reservoir adapted to receive and retain wound fluids which have leaked through channel 32 to the back surface of base sheet 14 of wound dressing component 12. Cover component 34 is essentially the same as the dressing described and claimed in my copending application, Ser. No. 461,598 adapted for placement directly on the wound, except that in the modification of this invention, it will be appreciated that the adhesive layer of the wound dressing of the aforementioned copending application to adhere the dressing to the skin is not necessary in the practice of the present invention.

As shown, the cover component 34 is of generally the same configuration as dressing component 12. The cover component 34 has a bottom sheet or film 36 which is shown to have a plurality of perforations 38 permitting passage of wound fluid through bottom sheet 36. Sheet 36 and base sheet 14 of dressing component 12 are sealed around their common periphery, to provide a barrier against ingress of bacteria or other external contaminants, as well as to preclude lateral escape of wound fluid through the edges of the dressing. While the seal may be a permanent one, e.g. by heat sealing, in a particularly preferred embodiment of this invention, sheets 36 and 14 are releasably secured around their common periphery by means of a suitable pressure-sensitive adhesive. In this preferred embodiment, when the reservoir is filled, the cover component may then be removed and replaced with another without removing the dressing component on the wound, thereby obviating the trauma associated with dressing removal which can adversely affect the healing process. An outer liquid- and bacteria-impermeable cover sheet 40 is sealed in liquid- and bacteria-tight relationship around its periphery to the periphery of perforated sheet 36 to define a chamber 42 in which is disposed a fabric reservoir 44 for receiving and retaining wound fluids diffusing from the upper surface of sheet 14 through the perforations 38 in sheet 36. As illustrated, the outer cover sheet 40 has one or more openings or windows 40a to permit egress of air from the interstices or voids in fabric reservoir 44. Each window or opening 40a is covered by an air-permeable bacterial barrier sheet material 46 of slightly larger dimensions than the dimensions of opening 40a. As shown, bacterial barrier sheet material 16 is sealed around its periphery to the edges of sheet 40 around opening 40a so as to prevent ingress of bacteria around the edges of the opening into chamber 42.

Figure 3:
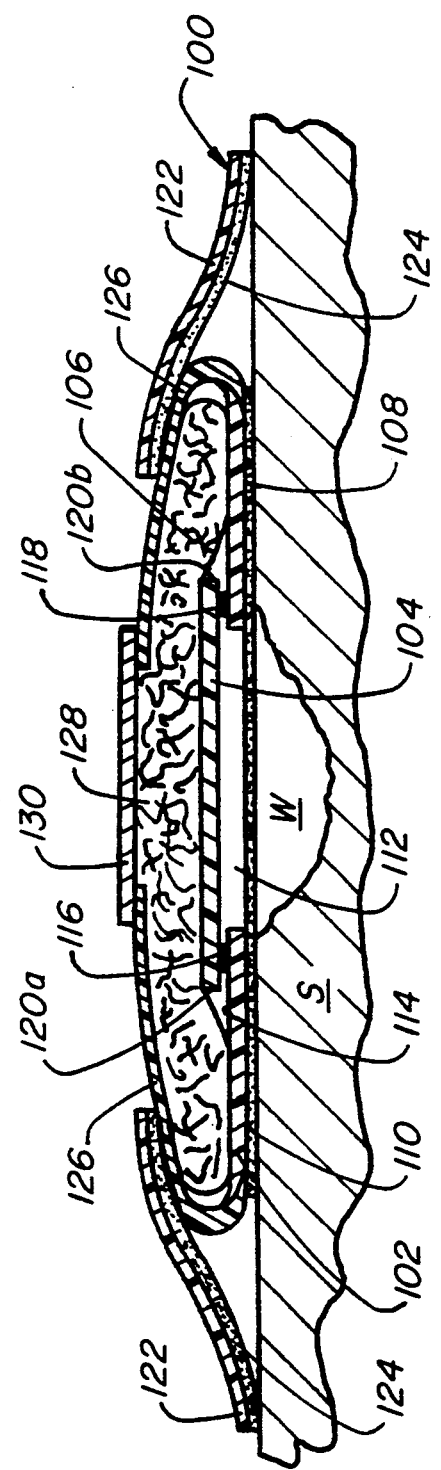
FIG. 3 is a sectional view similar to FIG. 2 illustrating an alternate embodiment of this invention.

FIG. 3 illustrates another embodiment of this invention, being a modification of the vented dressing shown in FIGS. 1-3 of the parent application, Ser. No. 337,591.

As shown in FIG. 3, the dressing, generally designated 100 has a base sheet 102, a vent sheet 104, and an absorbent fabric reservoir 106. The base sheet 102 has an adhesive 108 on its front surface 110 securing the dressing 100 to the skin S. The base sheet 102 has an opening 112 extending therethrough and the base sheet is shown to be secured to the skin with the opening 112 located over a wound W.

Vent sheet 104, which is preferably of a generally rectangular configuration, has a pair of opposed side edges (not shown in the sectional view) and a pair of opposed end edges 120a and 120b connecting the side edges. As shown, the vent sheet 104 is secured to the back surface 114 of the base sheet 102 along sealing lines 116 and 118, by heat sealing or adhesive means, extending along and adjacent the end edges 120a and 120b. In this configuration, vent sheet 104 covers the opening 112 of the base sheet 102, with the side edges being free of attachment from the base sheet, similar to the embodiment shown in FIGS. 1 and 2.

The fabric reservoir 106 is located over the back surface 114 of the base sheet 102 and over vent sheet 104.

Fabric reservoir 106 is shown to be secured by tape strips 122 having an adhesive 124 on the front surface thereof to the skin S of the patient. While so-called breathable or porous medical grade tape backings are well known, as are discontinuous adhesive layers, in accordance with this invention the tape backing will preferably be a continuous sheet material providing an effective bacterial barrier, and the adhesive layer 124 will preferably be continuous so as to provide an additional effective barrier against ingress of bacteria laterally along the skin line toward dressing 100.

The bacterial barrier is completed by the cover component to the dressing provided by liquid-and bacteria-impermeable cover sheet 126 having one or more windows or openings 128 covered by an air-permeable bacterial barrier sheet material 130 of slightly larger dimensions than the dimensions of the openings 128 in sheet 126, similar to the cover sheet arrangement shown in the embodiments of FIGS. 1 and 2. Also, as will be understood, the bacterial barrier sheet 130 is sealed around the periphery to the edges of sheet 126 around the edges of the opening 128; and sheet 126 is, in turn, sealed to sheet 114 around their common periphery, whereby the fabric reservoir is confined within a chamber effectively free from external contaminants, the chamber being defined by sheets 130, 126, 104 and 102, respectively. As in the embodiment illustrated in FIGS. 1 and 2, the seal is most preferably a releasable one, as by means of a pressure-sensitive adhesive, so as to permit replacement of the cover component without disturbing the wound by removal of the dressing. As shown, the adhesive tapes for securing the dressing to the skin beyond wound W are adhered to the outer surface of cover sheet 126 by means of pressure-sensitive adhesive layers 124.

The particular materials employed for preparing the various components of the dressing may be selected from those heretofore known in the art for providing their respective functions. Since such materials are well known and their selection will be a matter of choice within the expected judgment of the skilled worker in the light of the foregoing description, their selection per se accordingly comprises no part of this invention.

However, by way of illustration, base sheets 14 and 102, which may be on the order of 1–1.5 mils thick, may be constructed of a suitable, preferably moisture vapor permeable flexible polymeric material such as polyurethane, SARAN (trademark of Dow Chemical Company), a cellulose ester, etc.

Adhesive coatings 18 and 108 may be any of the so-called medical grade adhesive heretofore employed for application to the skin. Such known adhesives include the rubber-based, acrylic, vinyl ether and hydrocolloid pressure-sensitive adhesives. To provide a suitable bacterial barrier, they must be applied as a continuous layer around at least the entire periphery of the base sheet.

Vent sheets 20 and 104, which may be on the order of one mil thick, may also comprise a flexible polymeric material such as those heretofore mentioned for the base sheet.

The bottom sheet 36 of cover component 34 (FIGS. 1 and 2) may comprise any of the per se known perforated flexible films and may also be on the order of one mil thick. As examples of such films, mention may be made of polyurethane, cellulose acetate, cellulose triacetate, etc. While for purposes of illustration film or sheet 36 has been shown to be perforated, it will be appreciated that where found desirable or expedient to do so, suitable porous materials such as cellulose esters, vinyl polymers and the like may be employed in lieu thereof, including porous sheet materials which have been chemically treated or coated to make them more suitable for use in the contemplated wound dressings. Since the desired degree of porosity or permeability to wound exudate will vary according to such factors as the nature of the intended wound to be covered, the anticipated amount of exudate and/or the frequency of dressing changes contemplated, it is not susceptible to precise quantification. In any event, the selection of the particular permeability to wound exudate for a given dressing will be a matter of choice of design within the judgement of the skilled worker in the light of this description.

The opening 16 (FIG. 1) has been shown for purposes of illustration as being generally circular. However, the openings in the base sheet may be elongated or of any other suitable shape, as is shown and disclosed in the parent application. Moreover, as disclosed therein, a plurality of openings in the base sheet may be provided in lieu of a single opening. In any case, as will be appreciated, the opening or openings must be sufficient to permit passage therethrough into the dressing of excess wound fluid so as to inhibit pressure build-up and the heretofore discussed problems resulting therefrom.

Fabric reservoirs 44 and 106 may comprise any of the fabric materials heretofore employed for wound dressings to retain exudate, e.g. cotton, gauze sponges, absorbent pads such as those customarily used for abdominal surgery, and the like. If desired, they may additionally contain an antimicrobial agent such as chlorhexidine, although the use of such a reagent is not considered necessary.

Water-impermeable sheets 40 and 126 should of course also be impermeable to bacteria as well. They may, for example, be on the order of 0.5 to 1.0 mil thick and comprise a suitable polymeric material such as polyurethane, "Saran" (trademark of Dow Chemical), a polyolefin such as polyethylene or polypropylene, a polyester such as polyethylene terephthalate, etc. In any event, sheets 40 and 126 must be imperforate as well as being flexible and conformable.

Bacterial barrier 46 or 130 may comprise any of the per se known bacterial barrier air filters such as NUCLEOPORE, MILLIPORE, GELLMAN, etc.

As will be understood, in practice excess wound fluid or exudate will pass through the opening(s) in the base sheet covering the wound, leak through the vent sheet and then be wicked or diffuse into the fabric reservoir contained in an external contaminant-free environment which in turn prevents migration of bacteria and/or other contaminants down through the dressing to the wound. The air-permeable bacterial barrier covering the dressing permits egress of air from the voids or interstices of the reservoir while at the same time maintaining the external contaminant-free integrity of the drawing.

It is to be expressly understood that the wound dressings shown in the illustrative drawings are capable of various modifications without departing from the scope of the invention herein contemplated.

For example, since the known bacterial barrier sheets 46 and 130 are relatively expensive, the cover for the dressing has been shown to consist essentially of a conventional impermeable sheet material provided with an opening or window which is covered by the relatively more expensive bacterial barrier sheet. However, it is contemplated that the cover may instead comprise a single air-permeable, bacteria-and liquid-impermeable sheet material. Alternatively, the external sheet 44 or 106 may of course be provided with a plurality of windows covered in turn by a corresponding plurality of bacterial barrier sheets.

Other changes will be readily suggested in the light of the foregoing description.

By way of recapitulation, it will be seen that the present invention provides a vented wound dressing of the type described in the parent application, Ser. No. 337,591, the dressing having a fabric reservoir for receiving and retaining wound fluids, the reservoir being encased within outer walls which provide an effective barrier to external contaminants while at the same time permitting egress of air from within the interstices or voids of the fabric reservoir in order to optimize the amount of wound fluid which can be wicked diffused into the fabric reservoir. This optimizing of wicking in turn minimizes the frequency of dressing changes which may be required.

An important feature of the present invention is the ability, in the preferred embodiment, to replace the cover component and wound fluid reservoir without removing the base sheet covering the wound, which removal may cause injury to the healing skin and thereby impair the healing process.

Since it is not possible to ascertain whether the bacterial barrier precludes the presence of any bacteria within the reservoir so that it can be said to be totally bacteria-free, as used herein and in the appended claims, the term "effective barrier" is used, denoting a barrier which effectively precludes ingress of bacteria from the ambient atmosphere to said reservoir, whereby the reservoir and the chamber in which it is contained can be reasonably regarded as being safe from the danger of infection induced by the presence of bacteria entering the dressing from the ambient atmosphere.

Since certain changes may be made without departing from the scope of the invention herein contemplated, all matter contained in the foregoing description and drawing shall be taken as being illustrative and not in a limiting sense.

What is claimed for:

1. In a wound dressing comprising a base sheet having at least one opening adapted for placement over a wound, and vent means for providing controlled leakage of wound fluid along a path from said wound through each said opening of said base sheet, the vent means permitting passage of wound fluid therethrough while reducing evaporation through each said opening and thereby helping to insure a moist environment when excess would fluid is removed from the wound;

the improvement comprising a cover element secured to said dressing over said base sheet and said vent means, said cover element having wall members defining a chamber into which said wound fluids leaking through said vent means can wick or diffuse; a fabric reservoir having voids or interstices adapted for receiving and retaining said would fluids diffusing thereto within said chamber, the wall members defining said chamber providing an effective barrier against ingress of bacteria and other external contaminants, at least a portion of an outer wall member of said chamber being characterized as being both a bacterial barrier and as being air permeable, the air permeability of said at least portion being sufficient to permit egress of air from said voids or interstices within said reservoir, whereby to optimize the amount of fluids said reservoir can receive by diffusion or wicking through said dressing.

2. A wound dressing as defined in claim 1 wherein said vent means comprises a vent sheet secured to said base sheet over said opening.

3. A wound dressing as defined in claim 2 wherein said vent sheet has a raised portion defining at least one channel extending from the opening to an edge of said vent sheet.

4. A wound dressing as defined in claim 2 wherein said vent sheet has a pair of opposed side edges and a pair of opposed end edges, said vent sheet being secured to said base sheet at a location adjacent at least one of said edges, with the other of said edges being free of attachment to the base sheet, whereby to permit leakage of wound fluid diffusing through each said opening through said unattached edges.

5. A wound dressing as defined in claim 4 wherein said vent sheet is secured to said base sheet at a location adjacent each of said end edges.

6. A wound dressing as defined in claim 1 wherein each said opening in said base sheet is generally circular.

7. A wound dressing as defined in claim 2 wherein said base sheet contains a single said opening, said vent sheet has a pair of side edges and a pair of end edges connecting said side edges, and said opening is generally located between said edges of said vent sheet.

8. A wound dressing as defined in claim 1 wherein said base sheet has an adhesive layer for securing the base sheet over the wound.

9. A wound dressing as defined in claim 1 wherein said dressing has adhesive strips attached thereto for securing the dressing to the skin on opposed sides of said wound.

10. A wound dressing as defined in claim 1 wherein said chamber has a bottom wall member permeable to wound fluids and a periphery common with the base sheet, said bottom wall member and said base sheet being sealed together around their common periphery.

11. A wound dressing as defined in claim 10 wherein said bottom wall member comprises a substantially liquid-impermeable sheet material, said sheet material having a plurality of perforations permitting passage of said wound fluid therethrough to within said chamber.

12. A wound dressing as defined in claim 1 wherein said cover element is releasably secured to said dressing, whereby to permit removal and replacement of said cover element without removing said dressing from the wound.

13. A wound dressing comprising:
(1) a base sheet adapted for adhering to skin around the wound said base sheet having at least one opening for placement over a wound;
(2) a vent sheet seated on said base sheet overlying said opening, said vent sheet permitting leakage of wound fluid along a path from said wound through said opening and said vent sheet;
(3) a sheet permeable to said wound fluid positioned over said base and vent sheets;
(4) first securing means for securing said base and fluid-permeable sheets around their periphery;
(5) an outer cover element characterized as being a bacterial barrier, at least a portion of said cover element further being characterized as being air permeable;
(6) said outer cover element and said fluid permeable sheet being secured together around their periphery in spaced relationship by second securing means to define a chamber therebetween for receiving wound fluids diffusing from said surface of said base sheet through said fluid permeable sheet, said first and second securing means providing an effective barrier against ingress of bacteria and other external contaminants to within said chamber; and (7) a fabric material disposed within said chamber, said fabric material having voids or interstices providing a reservoir for receiving and retaining wound fluid diffusing or wicking to within said chamber through said fluid permeable sheet, the air permeability of said cover element being sufficient to permit egress of air from said voids or interstices within said reservoir, whereby to optimize the amount of fluids said reservoir can receive.

14. A wound dressing as defined in claim 13 wherein one of said securing means comprises a releasable pressure-sensitive adhesive, whereby to permit removal and replacement of said reservoir without requiring removal of said base sheet from said wound.

15. A wound dressing as defined in claim 14 wherein said vent sheet has a pair of opposed side edges and a pair of opposed end edges, said vent sheet being secured to said surface of said base sheet at a location adjacent two of said edges, the other said edges being free of attachment whereby to permit leakage of wound fluid through said unattached edges.

16. A wound dressing as defined in claim 15 wherein said vent sheet has a raised portion defining at least one channel extending from said opening(s) to an edge of said vent sheet.

17. A wound dressing as defined in claim 16 wherein said outer cover element comprises a liquid-impermeable first sheet material having at least one opening or window through which air can pass, each said opening or window being covered by a second sheet material of slightly larger dimensions than the dimensions of said window or opening it covers, each said second sheet material being sealed to said first sheet material to provide an effective bacterial barrier around the periphery of each said opening or window, each said second sheet material comprising an air-permeable bacterial barrier.

18. A wound dressing as defined in claim 17 wherein said fluid permeable sheet comprises a substantially liquid-impermeable sheet material having a plurality of perforations rendering said sheet fluid permeable.

19. In a wound dressing comprising a base sheet having at least one opening adapted for placement over a wound, and vent means for providing controlled leakage of wound fluid along a path from the wound through each said opening of the base sheet;
the improvement comprising a cover element secured to said dressing over said base sheet and said vent means, said cover element having wall members defining a chamber into which said wound fluids leaking through said vent means can wick or diffuse; a fabric reservoir having voids or interstices adapted for receiving and retaining said wound fluids diffusing thereto within said chamber, the wall members defining said chamber providing an effective barrier against ingress of bacteria and other external contaminants, the wall members including an outer wall member comprising a liquid-impermeable first sheet material having at least one opening or window through which air can pass, each said opening or window being covered by a second sheet material of slightly larger dimensions then the dimensions of said window or opening it covers, each said second sheet material being sealed to said first sheet material to provide an effective bacterial barrier around the periphery of each said opening or window, each said second sheet material comprising an air-permeable bacterial barrier, the air permeability of the outer wall second sheet material being sufficient to permit egress of air from said voids or interstices within said reservoir, whereby to optimize the amount of fluids said reservoir can receive by diffusion or wicking through said dressing.

20. A wound dressing as defined in claim 19 wherein said vent means comprises a vent sheet secured to said base sheet over said opening.

21. A wound dressing as defined in claim 20 wherein said vent sheet has a raised portion defining at least one channel extending from the opening to an edge of said vent sheet.

22. A wound dressing as defined in claim 20 wherein said vent sheet has a pair of opposed side edges and a pair of opposed end edges connecting said side edges, with the other of said edges being free of attachment to the base sheet, whereby to permit leakage of wound fluid diffusing through said opening(s) through said unattached edges.

23. A wound dressing as defined in claim 22 wherein said vent sheet is secured to the inner surface of said base sheet at a location adjacent each of said end edges.

24. A wound dressing as defined in claim 19 wherein each said opening in said base sheet is generally circular.

25. A wound dressing as defined in claim 19 wherein said base sheet contains a single said opening, said vent sheet has a pair of side edges and a pair of end edges connecting said side edges, and said opening is generally located between said edges of said vent sheet.

26. A wound dressing as defined in claim 19 wherein said base sheet has an adhesive layer on the outer surface thereof for securing the base sheet to the skin.

27. A wound dressing as defined in claim 19 wherein said dressing has adhesive strips attached thereto for securing the dressing to the skin on opposed sides of said wound.

28. A wound dressing as defined in claim 19 wherein said chamber has a bottom wall member permeable to wound fluids, said bottom wall member and said base sheet being sealed together around their common periphery.

29. A wound dressing as defined in claim 28 wherein said bottom wall member comprises a substantially liquid-impermeable sheet material, said sheet material having a plurality of perforations permitting passage of said wound fluid therethrough to within said chamber.

30. A wound dressing as defined in claim 19 wherein said cover element is releasably secured to said dressing, whereby to permit removal and replacement of said cover element without removing said dressing from the wound.

* * * * *